US 8,545,505 B2

(12) United States Patent
Sandstrom et al.

(10) Patent No.: US 8,545,505 B2
(45) Date of Patent: Oct. 1, 2013

(54) LOW FRICTION ROD PERSUADER

(75) Inventors: Jason P. Sandstrom, Marquette, MI (US); Jeffrey A. Hoffman, Anchorage, AK (US); Jeffrey D. Vlahos, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 0 days.

(21) Appl. No.: 12/977,968

(22) Filed: Dec. 23, 2010

(65) Prior Publication Data

US 2011/0257692 A1    Oct. 20, 2011

Related U.S. Application Data

(60) Provisional application No. 61/295,625, filed on Jan. 15, 2010.

(51) Int. Cl.
*A61B 17/70*    (2006.01)
(52) U.S. Cl.
USPC .................................................. 606/86 A
(58) Field of Classification Search
USPC ............... 606/86 A, 99, 104, 246–279, 916; 81/451–453
See application file for complete search history.

(56) References Cited

U.S. PATENT DOCUMENTS

| | | | |
|---|---|---|---|
| 2004/0147937 A1* | 7/2004 | Dunbar et al. | 606/99 |
| 2004/0267275 A1* | 12/2004 | Cournoyer et al. | 606/99 |
| 2006/0247630 A1* | 11/2006 | Iott et al. | 606/61 |
| 2008/0077135 A1* | 3/2008 | Stad et al. | 606/61 |
| 2008/0243133 A1* | 10/2008 | Heinz | 606/104 |
| 2008/0243134 A1* | 10/2008 | Limberg et al. | 606/104 |
| 2008/0243190 A1* | 10/2008 | Dziedzic et al. | 606/278 |
| 2009/0105712 A1* | 4/2009 | Dauster et al. | 606/99 |
| 2009/0157125 A1* | 6/2009 | Hoffman et al. | 606/86 A |
| 2009/0182382 A1* | 7/2009 | Justis et al. | 606/279 |
| 2009/0228053 A1* | 9/2009 | Kolb et al. | 606/86 A |
| 2009/0318972 A1* | 12/2009 | Jackson | 606/264 |
| 2011/0087298 A1* | 4/2011 | Jones | 606/86 A |

* cited by examiner

*Primary Examiner* — Jan Christopher Merene
*Assistant Examiner* — Michelle C Eckman
(74) *Attorney, Agent, or Firm* — Fitch, Even, Tabin & Flannery LLP

(57) ABSTRACT

Instruments are provided for shifting elongate members, such as spinal rods, with respect to coupling members of spinal fixation systems. The instruments include a low friction drive mechanism having one or more rolling elements that ride along a helical groove or track in order to transform rotational movement of a drive member into linear shifting of a reducer member that shifts the elongate member. A one-way locking mechanism may be provided to selectively prevent unwanted counter-rotation of the low friction drive mechanism. The one-way locking mechanism may include annular ratchet teeth arranged on the exterior of the drive member and a ratchet pawl located adjacent to the teeth and selectively engageable therewith.

9 Claims, 12 Drawing Sheets

LOW FRICTION ROD PERSUADER

CROSS-REFERENCE TO RELATED APPLICATION

This application claims the benefit of U.S. Provisional Application 61/295,625, filed Jan. 15, 2010, which is hereby incorporated herein by reference in its entirety.

FIELD OF THE INVENTION

This invention pertains generally to medical instruments and more specifically to spinal implant insertion instruments for spinal fixation systems.

BACKGROUND OF THE INVENTION

Various devices for internal fixation of bone segments in the human or animal body are known in the art. One type of system is a pedicle screw system, which is sometimes used as an adjunct to spinal fusion surgery, and which provides a means of gripping a spinal segment. A conventional pedicle screw system comprises a pedicle screw anchor and a rod-receiving device or coupling member. The pedicle screw anchor includes an externally threaded stem or shank and a head portion. The rod-receiving device couples to the head portion of the pedicle screw and receives an elongate member such as a spinal rod. Two such systems are inserted into respective vertebrae and adjusted to distract and/or stabilize a spinal column, for instance during an operation to correct a herniated disk. The pedicle screw does not, by itself, fix the spinal segment in place, but instead operates as an anchor point to receive the rod-receiving device, which in turn receives the rod. Securing the rod to two or more vertebrae limits the position of the vertebrae with respect to one another, allowing the associated region of the spine to heal or correcting improper positioning of the vertebrae. One goal of such a system is to substantially reduce and/or prevent relative motion between spinal segments that are being fused.

Most pedicle screw systems are "top loading," wherein a spinal rod is positioned above and perpendicular to the pedicle screw anchor, and then lowered into a channel of the rod receiving device that faces upward from the pedicle screw anchor. Many pedicle screw systems include a threaded locking member that is rotatably inserted into the rod-receiving device on top of the rod after the spinal rod is seated therein in order to fix the position of the spinal rod. Threadless locking members with flanges that are rotated into place to interlock with the rod-receiving device have also been disclosed, such as in U.S. Pat. No. 7,141,051 and U.S. Patent Application No. 2007/0055235. Spinal fixation systems including locking components that require non-rotational linear shifting (such as along the axis of the rod-receiving device) for locking thereof also are known alternatives to utilizing rotatable locking members. Such linearly locking spinal systems are disclosed, for example, in United States Patent Application 2007/0225711, as well as U.S. Provisional Application Nos. 60/784,674 and 60/981,821. These systems include an anchor member (e.g., a screw or hook), a compressible inner tulip member that receives a spinal rod and a pedicle screw head snap-fit thereto, a rigid outer tulip that shifts axially over the inner tulip to compress the inner tulip tightly onto the screw head, and a cap member axially inserted between portions of the inner and outer tulip member to compress the inner tulip about the rod.

Regardless of the manner in which the locking member operates, top loading pedicle screw systems (and other top loading fixation systems such as hook devices) are best manipulated with an instrument capable of grasping the rod receiving device and "reducing" the spinal rod within the rod receiving device (forcing the spinal rod downward to a seated position within the rod-receiving device). Forces imparted on the fixation system and spinal rods by the anatomy of the patient's back, including the positioning and rotation of vertebrae that are to be connected by the fixation system, ordinarily must be overcome to correctly align multiple rod-receiving devices and a spinal rod. As a consequence, significant force must often be applied in order to shift the spinal rod into a fully seated position within the rod-receiving device, allowing the surgeon to correctly secure a locking member to the device and lock the spinal rod therein. Thus, an instrument that can provide a surgeon with a mechanical advantage in shifting the spinal rod into the rod-receiving device is of great benefit. If desired, the same device may also be used to insert and lock the locking member during or after reduction of the spinal rod.

Prior art reducer instruments are often bulky, such as the device disclosed in U.S. Patent Application No. 2003/0225408 which has a side-mounted, lever-actuated clamping mechanism that is secured in position by a laterally-extending rack device. Other devices, such as the device disclosed in U.S. Patent Application No. 2009/0157125, rely on a threaded drive system which requires continual rotation of a drive portion to shift the spinal rod and may have problems with binding of parts. The friction inherent in such threaded drive systems often makes them less than ideal to operate. In addition, cleanability of prior art instruments is often also a concern, since they can have a number of moving parts that may become clogged with blood, tissue, or other materials. Therefore, improved tools for reducing spinal rods and inserting locking members into rod-receiving members are desired.

SUMMARY OF THE INVENTION

Reducing instruments are provided herein that mechanically assists a surgeon in positioning a spinal rod in place over the coupling device and provide the surgeon with mechanical leverage to adjust the elongate member, yoke member, and anchor member into the appropriate position for correcting spinal defects. In accordance with one aspect of the invention, a low friction rod reducing instrument is provided having a threadless drive system that transfers rotational movement of a drive actuator into linear motion of a reducing member through a rolling camming interface. For instance, rolling elements that roll through a guide track of a drive member may be coupled to the reducing member to form an interface between the two members that transfers rotational motion of the drive member into linear motion of the reducer member with significantly less friction than a threaded drive system.

A one-way locking system may also be provided in the instrument in order to selectively prevent unwanted backward motion of the low friction drive mechanism. The ease of use of the helical drive system described herein may lead to unwanted reverse rotation of the drive system due to the reduced friction involved. In other words, after advancing one of the members, the low friction of the rolling drive system may tend to allow the advanced reducer member to retract back away from the advanced position thereof when a load is applied to the instrument. For instance, the forces applied to the elongate member that resist "reducing" or repositioning of the elongate member may be able to reverse the direction of the instrument's reducer member unless the user of the instrument continuously provides force to the drive mechanism. Therefore, it may be desirable to include in the instrument a one-way locking device, such as a ratchet mechanism, to maintain the positioning of the various members of the instrument when the drive mechanism is released. For instance, the drive member with the helical recess may have a portion equipped with teeth on its exterior in an annular arrangement, with a pawl mechanism positioned adjacent the teeth in order to prevent rotation of the drive member in a backward direction but allow rotation of the drive member in the forward direction. In one aspect of the invention, the one-way locking device is a ratchet mechanism that includes a set of ratchet teeth, a pawl for interacting with the ratchet teeth, and a moveable ratchet engagement member that holds the pawl and can be shifted between engaged and disengaged positions.

Whereas in prior art ratchet systems a pawl binds against the teeth of a ratchet mechanism to prevent backward motion and requires relief from any load placed upon the teeth prior to pivoting the pawl out of the way to disengage the ratchet mechanism, positioning the ratchet pawl on a moveable ratchet engagement member capable of shifting the entire pawl away from the ratchet teeth advantageously provides the ratchet mechanism with the ability to engage and disengage even when under a heavy load.

Typically, the coupling devices of a bone fixation system will include slits or channels for receiving the elongate member, and the reducer instrument attaches to the exterior of the coupling device in a manner which allows it to direct the elongate member into the slit or channel and then force the rod toward the end of the slit or channel to fully reduce the elongate member within the coupling device. The instrument may be designed to fully reduce the elongate member into the coupling device prior to introduction of a locking member therein for final locking of the elongate member within the coupling device, or may be designed to reduce the elongate member concurrently with introduction of the locking member into the coupling device.

To accomplish reduction of the elongate member prior to introduction of the locking member, the body of the instrument may be completely cannulated to allow the introduction of a separate locking member insertion instrument. Alternatively, the cap locking mechanism may be configured as a component of the instrument that is separate from the reducing mechanism, and may even be configured so that the cap locking mechanism is also responsible for simultaneously reducing the rod, such as in a device wherein the cap locking portion drives the cap downward against the rod in order to shift the rod into the slit or channel of the coupling device. In another aspect of the invention, torque and counter torque handles may be provided to allow the application of increased force to drive the spinal rod toward and into the coupling device.

In one aspect of the invention, the reducer instrument may have a clamp member for selectively securing the coupling device to the instrument, a reducer member for shifting the elongate member into place within the coupling device, and optionally a locking member inserter to secure a locking member to the coupling device in order to capture the elongate member therein. One or more of the members, or a separate drive actuator member, may be provided with a helical recess on its inner or outer surface to interact with a rolling element coupled to another member in order to transfer rotational motion of one portion of the instrument into linear motion of the same portion or another portion of the instrument. In this manner, the instrument responds to manipulation in much the same manner as a threaded drive system, although friction is greatly reduced due to the presence of rolling elements instead of complementary threads.

The need for lubrication is thereby minimized or eliminated, and cleanability of the instrument is improved since the drive system can be fully sealed.

The drive system may include a motor assembly, although manual operation of the apparatus will primarily be described herein. Examples of motor assemblies that could be used are an electric motor, hydraulic motor, or pneumatic motor.

The components of the reducer instrument may be generally cylindrical in shape to minimize the profile of the apparatus, reducing the size of the incision necessary for surgery and subsequently reducing the recovery time of the patient. In alternative embodiments, the components can have other configurations such as hexagonal prism or rectangular prism configurations.

In one form, the clamp member may be located concentrically within the reducer member so that shifting of the reducer member simultaneously shifts the elongate member and exerts an inwardly-directed force onto the clamp member in order to tightly secure the clamp member to the coupling device. For instance, the reducer member may be configured as a sleeve that slides downward around a clamp member having multiple prongs, forcing the prongs toward one another to clamp against a coupling device.

Alternatively, the reducer member or other portions of the instrument may be configured so that retraction of the reducer member operates to release the clamp member. For instance, the clamp member may be configured so as to be biased toward a clamped position, with elements linked to the reducer member configured to force clamping elements of the clamp member apart as the reducer member shifts away from the coupling device. In this configuration, retracting the reducer member forces the clamp member open, releasing any coupling device located therein and allowing a new coupling device to be disposed between the clamp elements of the clamp member. For instance, the clamp member may be formed as a split sleeve with slits and a central opening sized and configured to receive a coupling device, and the reducer member may be configured as a sleeve sized to surround the clamp member and fitted with pins that slide through the slits in the clamp member, thereby causing splaying of the clamp member at certain positions.

In one preferred form, the reducer instrument includes an elongate stationary clamp member; a rotatable drive actuator operatively coupled to the clamp member; a reducing member operatively coupled to the clamp member and drive actuator so that it is shiftable along the axis of the elongate clamp member; and optionally a cap inserter. In a preferred form, the reducing member includes a sleeve portion surrounding the clamp member, while the drive member is positioned within an axial bore of the clamp member, and has a helical recess about its outer surface. The helical recess of the drive member is sized and configured to receive rolling elements that extend through elongate openings of the clamp member and are linked to the reducing member disposed about the outer surface of the clamp member. Elongate openings in the clamp member may be positioned so as to allow the rolling elements to contact both the helical recess of the drive member and the interior surface of the reducing member even though the clamp member is disposed between the two. In this form, rotation of the drive member guides the rolling elements along the helical recess, shifting them through the elongate opening in the clamp member and, due to their linkage to the reducing member, causing the reducing member to shift along the exterior of the clamp member. In another preferred form, a ratchet assembly is provided in order to allow rotation of the drive member in one direction but prevent rotation of the drive member in the opposite direction unless the ratchet assembly is disengaged.

The instruments described herein may be adapted for use with particular coupling devices, such as those described in U.S. Pat. No. 7,141,051 (issued on Nov. 28, 2006), U.S. Patent Application 2008/0045955 (Ser. No. 11/839,843), or U.S. Patent Application 2007/0225711 (Ser. No. 11/726,868), all of which applications are hereby fully incorporated by reference as if fully set forth herein. The instrument, anchor member, and coupling device may all be fully cannulated so that a wire can be passed therethrough for minimally invasive surgical (MIS) systems. In such systems, a guide wire is attached to a predetermined point on the surface of a bone, and then elements of an implant such as the coupling device mentioned above are passed around the guide wire so that the guide wire directs the implant elements to the predetermined point on the bone. Similarly, the instrument for reducing an elongate member into the coupling device also can be cannulated, i.e. contain a pathway through the center of the tool so that the aforementioned guide wire threaded through the anchor and coupling device can be threaded through the body of the instrument and is able to direct implantation or manipulation of the system without interfering with the operation of the tool. The accuracy gained by use of such a guide wire reduces the amount of tissue affected by the surgical procedure and reduces recovery time for the patient.

The reducer instrument can be made from any suitable, structurally strong material. Preferably, the reducer instrument, especially the exterior portion is constructed of metallic materials such as stainless steel or other metal alloys such as titanium. Coatings, such as chrome coatings, and lubricants may also be applied in order to reduce friction and otherwise enhance function of the instrument. The reducer instrument apparatus also can be made from non-conductive material such as various plastics, including polyetheretherketone (PEEK) and related compounds, in order to avoid conduction of electricity. The reducer instrument also can be made from ceramics that also provide non-conductive characteristics. Combinations of the foregoing materials also can be used that combine the properties of the said materials, i.e. metals combined with non-conductive materials.

DETAILED DESCRIPTION

Figure 1:
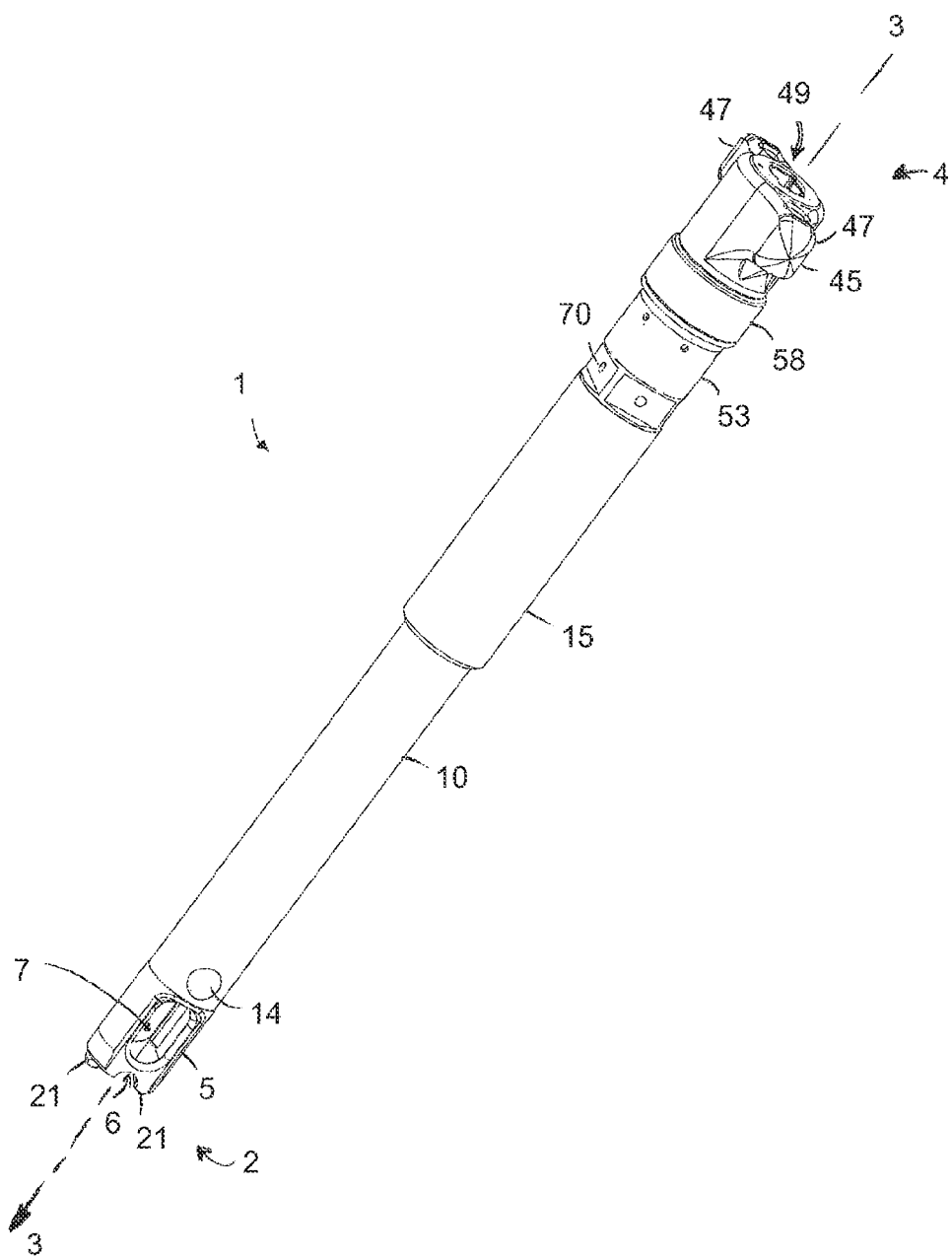
FIG. 1 is an exterior perspective view of one embodiment of an elongate reducer instrument.

FIG. 1 illustrates a particular embodiment of the reducer instrument disclosed herein. The exemplary instrument includes a central clamp member with clamping prongs 21 designed to engage a coupling device such as a pedicle screw assembly, a reducer sleeve 10 with a head portion 5 that is contoured to abut a spinal rod and shift the rod along the instrument axis 3, and a rotatable actuator 45 configured to shift the reducer sleeve 10 axially when rotated. Rotatable actuator 45 includes two lateral flanges 47 in order to form a T shape for easy manipulation by a surgeon. A ratchet system, which minimizes or substantially prevents unwanted backward rotation of the handle 45 when engaged, is located within the instrument and hidden from view by a ratchet housing 53 and a ratchet cover 58.

The reducer head portion 5 of the exemplary instrument includes a reducing surface 6 formed as a semi-cylindrical notch designed to match the contour of the spinal rod to be reduced, and also includes a window 7 to assist in visualization of the coupling member that is received therein and secured by the clamping prongs 21. A bumper material (or the like) could be positioned at the end of the head portion 5 to prevent accidental notching of the spinal rod as the head portion 5 drives downward and exerts force against the rod. In addition, a holding mechanism such as a spring clip or friction fit arrangement could be included with the head portion to secure the spinal rod during the reduction procedure.

In use, the instrument 1 is secured to a coupling device implanted into a vertebra by disposing the coupling device between clamping prongs 21. The actuator handle 45 is rotated to shift the reducer sleeve 10 and its attached reducing head 5 toward the distal end 2 of the instrument 1. As shown in FIG. 1, the reducing sleeve 10 and head 5 are in the fully extended position, shifted to their maximal point toward the distal end 2 of the tool. In this state, the reducing head 5 ensures that the clamping prongs 21 cannot splay outward, thus making the instrument capable of tightly securing a coupling device between the clamping prongs 21. At this point, the reducing surface 6 is also positioned so that spinal rod contacting the reducing surface 6 would be fully seated within a coupling device trapped between the clamping prongs 21 retracting the reducing sleeve 10 causes pins 14 coupled thereto to splay apart the clamping prongs 21, releasing the coupling device.

The actuator 45 may also be formed with a variety of different shapes as long as the surgeon is able to rotate the actuator sufficiently to cause desired shifting of the reducer member 10. For instance, the rotatable actuator 45 may be formed in an L shape or given a cylindrical or polygonal shape. In the exemplary instrument, a polygonal interface 60 for a counter torque handle is supplied. By securing a wrench-like counter torque handle to the interface 60, the surgeon may stabilize the position of the instrument 1 while rotating the rotatable actuator 45.

Since the spinal rod is fully seated in the coupling device when the reducer sleeve 10 and reducer head 5 reach the positions shown in FIG. 1, a locking member, such as a locking cap, may be inserted at that point into the coupling device and over the spinal rod, locking the spinal rod in place. The exemplary instrument of FIG. 1 is designed to be fully cannulated, as described below, and therefore allows for a separate locking member insertion instrument to be introduced through the axial bore 49 in the rotatable actuator 45.

The bore 49 leads to axial bores through the other components of the instrument, as described below. In the illustrated embodiment, the separate locking member insertion instrument may slide into the bore 49, although in other embodiments the insertion instrument may be introduced in other manners, such as rotationally via a threaded drive system or a ball screw system. As the locking member reaches the coupling device trapped between the clamping prongs 21, the user will be able to see the orientation and axial positioning of the locking member through the window 7 in the reducer head portion 5. This allows the user to manipulate the locking member inserter as necessary at the proximal end 4 of the instrument, such as by rotating or linearly shifting the locking member inserter as it is disposed within the reducer instrument in order to properly position the locking member, which can be seen through the window 7.

Figure 2:
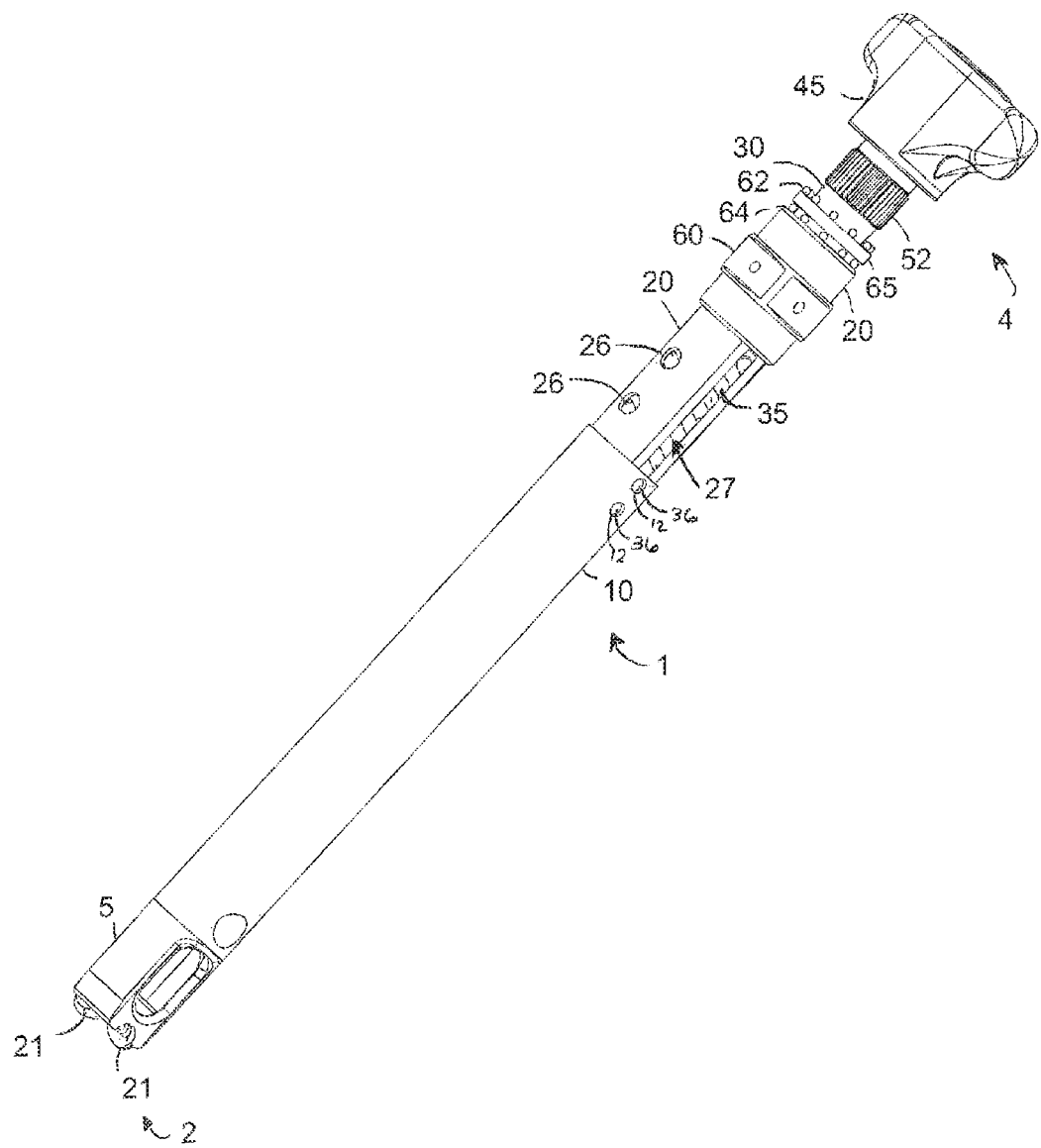
FIG. 2 is a perspective view of the instrument of FIG. 1 with certain exterior portions removed to reveal portions of a drive mechanism and ratchet mechanism.

The axial shifting of the reducer sleeve 10 is accomplished through a rolling interface between a rotatable actuator 30 linked to the actuator handle 45 and the internal surface of the reducer sleeve 10. This interface is shielded by a cover sleeve 15, which prevents dust, dirt, and other debris from clogging the interface. This interface is better illustrated by FIGS. 2 and 3. In FIG. 2, the instrument 1 is shown with the cover sleeve 15 removed. In addition, several components of a ratchet subassembly including a ratchet housing 53 and ratchet cover 58 have been removed from the proximal portion 4 of the instrument (the portion closest to the surgeon). The ratchet system of the instrument prevents counter-rotation of the actuator 45 and drive member 30 when engaged, and will be described in greater detail below. The annular ratchet teeth 52 exposed by removal of the ratchet cover 58 are integral to a drive member 30 that is coupled to the actuator handle 45. The drive member 30 is disposed concentrically within the clamp member 20, and is rotatable with respect thereto. In order to assist rotation of the drive member 30, two circular arrays of ball bearings 62 and 64 are provided. The ball bearings are disposed on both sides of an annular flange 65 protruding from the drive member 30. The lower bearing array 64 permits smooth rotation between the drive member 30 and the proximal end of the clamp member 20. The upper bearing array 62 facilitates smooth rotation between the drive member 30 and a ratchet housing that is normally disposed about the ratchet teeth 52. The drive member also includes a helical groove 35, which can be seen in FIG. 2 through an elongate opening or slit 27 in the clamp member 20.

The reducer sleeve 10 is disposed about the exterior of the clamp member 20. The reducer sleeve 10 is operatively coupled to the rotatable drive member 30 through rolling elements 36 which in the illustrated embodiment are spherical elements 36. These spherical elements are partially disposed in circular openings 12 in the reducer sleeve 10, and extend inward through the slit 27 in the clamp member and into the helical groove 35 of the rotatable drive member 30. Thus, as the rotatable drive member 30 is rotated the spherical elements will travel along the track created by the helical groove 35. Since the spherical elements 36 are confined to the axial slits 27 in the clamp member, rotation of the drive member 30 causes the spherical elements 36 to shift axially along the slit 27, which acts as a vertical guide track as the spherical elements 36 ride through the helical track formed by the annular groove 35. Being partially disposed in the circular openings 12 of the reducing sleeve 10, vertical movement of the rolling spherical elements 36 in turn causes axial shifting of the sleeve 10. Rotation of the handle 45 and associated drive member 30 in a first direction causes shifting of the spherical elements 36 and associated sleeve 10 toward the distal end of the instrument 2, while rotating the handle 45 in the opposite direction causes shifting of the spherical elements 36 and sleeve 10 toward the proximal end of the instrument, retracting the reducing sleeve 10 and reducer head 5. The continuous rolling of the spherical elements 36 as they interact with the helical guide track 35 of the drive member 30, vertical guide track 27 of the stationary clamp member 20, and openings 12 of the reducer member 10 minimizes friction in the system and thereby allows the surgeon to easily and quickly advance the reducer member 10.

Figure 3A:
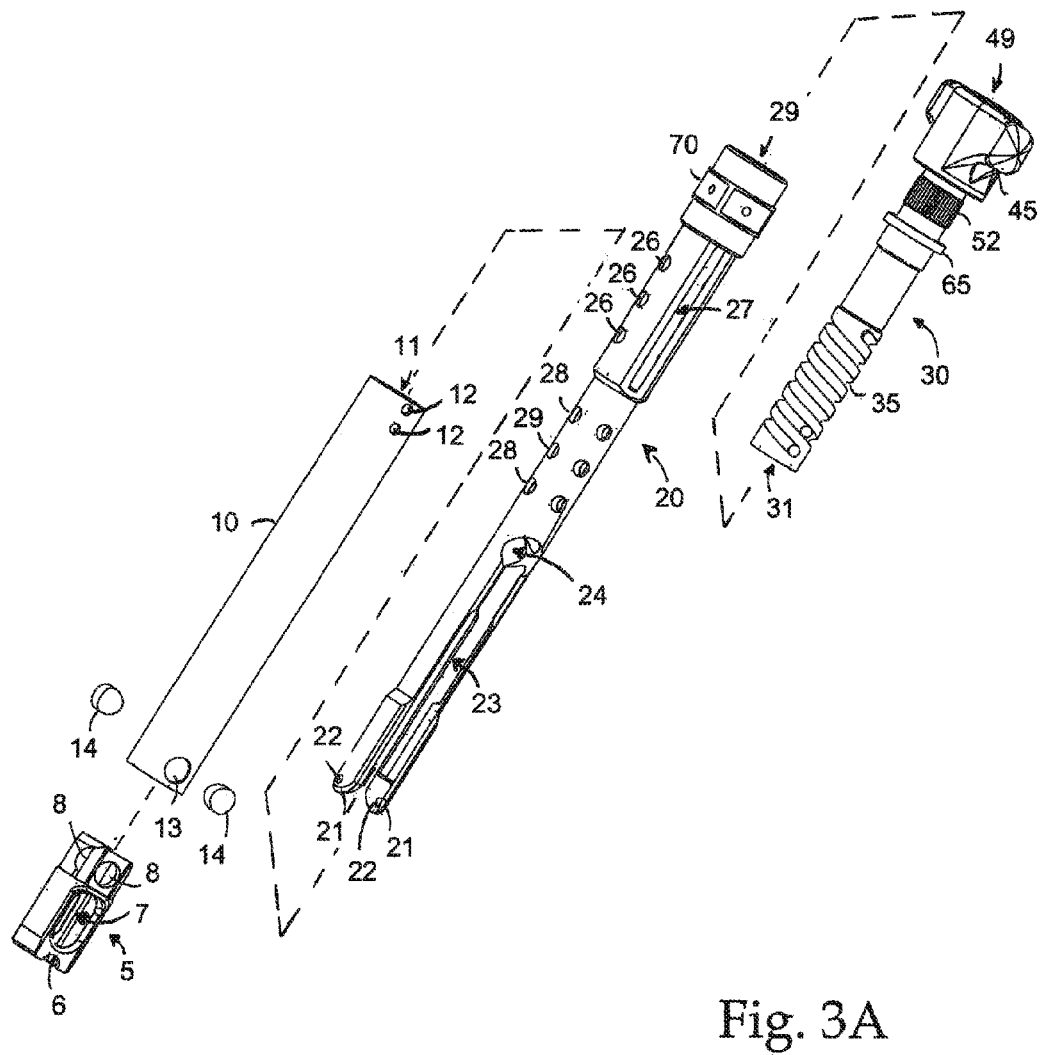
FIG. 3A is an exploded perspective view of the instrument portions shown in FIG. 2.

The primary components of the aforementioned drive coupling are shown in FIG. 3A in a disassembled state. In the illustrated form the drive member 30, clamping member 20, reducer sleeve 10, and reducer head portion 5, are all hollow generally cylindrical elements that are positioned relative to one another so as to share a common axis. The drive member 30 includes an actuator handle 45, an annular array of ratchet teeth 52, a bearing flange 65, and a helical recess 35 that forms part of a ball screw arrangement. An opening 49 at the top of the actuator handle 45 leads to an axial bore 31 running the entire length of the drive member 30. The lower portion of the drive member 30, which includes the helical recess 35, is placed within a bore 29 at the top of the clamp member 20. The lower part of the drive member therefore rests in a slightly widened portion of the clamp member 20, so that the helical recess 35 of the drive member 30 is positioned behind the slit 27 and openings 26 of the clamp member 20. When the drive member 30 is positioned within the bore 29 of the clamp member 20, the bearing flange 65 rests slightly above the top end of the clamp member 20. This allows for an array of ball bearings 64 (FIG. 2) to be positioned between flange 65 and the top of the clamp member 20. These ball bearings facilitate rotation between the drive member 30 and the clamp member 20.

The clamp member 20, like the drive member 30, is relatively cylindrical in shape and hollow so that a bore 29 runs axially through the entirety of the member. A series of openings 26 and 28 are provided in the clamp member in order to reduce the overall weight of the instrument. The clamp member 20 includes at its distal end two prongs 21 formed by a forking of the body of the clamp member 20. A gap 23 is formed between the two prongs 21 which allows the prongs to resiliently deflect outwardly an inwardly. A circular gap enlargement 24 at the top of the gap 23 reduces the stress on the clamp member 20 when the prongs 21 are splayed apart. The prongs 21 may be equipped with holding pegs 22 or other features that are shaped to mate with the exterior of a coupling device that is to be secured and manipulated by the instrument. The clamp member 20 is received in an axial bore 11 of the reducer sleeve 10.

The reducing sleeve 10 includes circular openings 12 designed to hold spherical rolling elements. These spherical rolling elements are also sized and configured to fit within the helical recess 35 of the drive member 30, and fit within the slit 27 of the clamping member 20. The spherical rolling elements thus link the drive member 30 and the sleeve 10 through the axial slit 27 of the clamp member 20. At its opposite end, the sleeve 10 includes openings 13 spaced diametrically opposite one another and each sized to receive a deflection pin 14. The deflection pins 14 are also sized to be received in openings 8 of the reducer head portion 5. Thus, the pins 14 are capable of securing the reducer head portion 5 to the reducer sleeve 10 when the openings 8 and the head portion 5 and the openings 13 in the sleeve portion 10 are aligned with one another. The deflection pins 14 also serve to manipulate the clamping mechanism of the instrument. As the drive member 30 is rotated in a reverse direction to retract the reducer sleeve 10, the sleeve will shift towards the upper end (proximal end) of the instrument. As the pins 14 move along with the sleeve 10, they slide linearly through the gap 23 between the clamping prongs 21. The prongs 21 and gap 23 between them may be configured as shown so that the gap 23 narrows towards its top and the pins 14 may be sized so that as they reach this narrowed portion of the gap 23, the clamping prongs 21 are splayed slightly outward. Conversely, rotation of the drive member 30 in the opposite, forward direction shifts the reducer sleeve 10 toward the distal end of the instrument, so that the deflection pins 14 are positioned in a wider portion of the gap 23 and no longer cause splaying of the clamping prongs 21. Further, the presence of the sleeve 10 about the exterior of the clamping prongs 21 assures that the prongs cannot deflect outward, thus tightly clamping any coupling device trapped between the prongs 21.

Figure 3B:
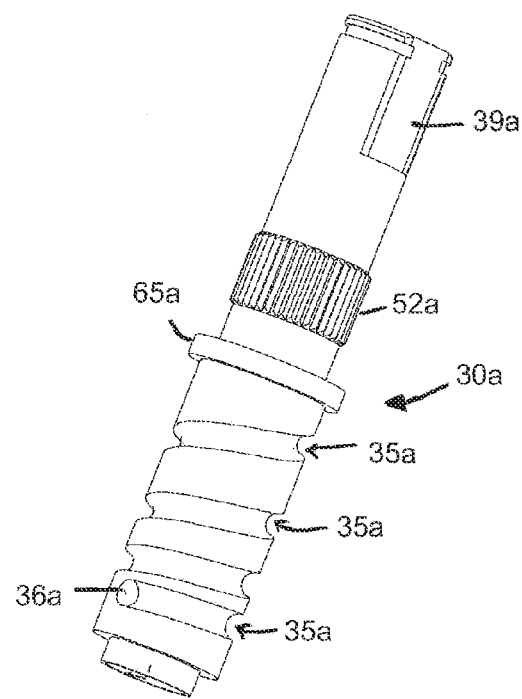
FIG. 3B is a perspective view of an alternative drive member for the instrument shown in FIG. 3A.

An alternative drive member 30a is illustrated in FIG. 3B. This drive member has a helical groove 35a with a varying pitch, so that the vertical distance traveled by the rolling element 36a disposed in the groove 35a with a set degree of rotation of the drive member 30a changes depending on the position of the rolling element 36a. As a result, a given degree of rotation of the drive member results in a different amount of linear shifting of the reducer member 10 depending on the positioning of the reducer member. In the illustrated embodiment, the pitch of the groove 35a is shallower toward the distal end of the drive member so that as the reducer sleeve approaches its fully extended position the reducer sleeve advances at a decreased rate, allowing the surgeon to more easily make fine adjustments at the end of the reduction procedure. The more pronounced pitch at the top end of the helical groove, on the other hand, allows the reducer member 10 to be advanced quickly to a position where it is close to engaging the rod. While the more pronounced pitch in this section of the groove 35a does not provide as great a mechanical advantage to the surgeon, the force that the instrument must exert to shift a spinal rod is usually much lower further from the seated position, and increase as the rod becomes more fully reduced. Therefore, the varying pitch of the helical groove 35a illustrated in FIG. 3B allows the instrument to be rapidly adjusted at positions or distances where it is not necessary for the instrument to generate large amounts of force.

Figure 4:
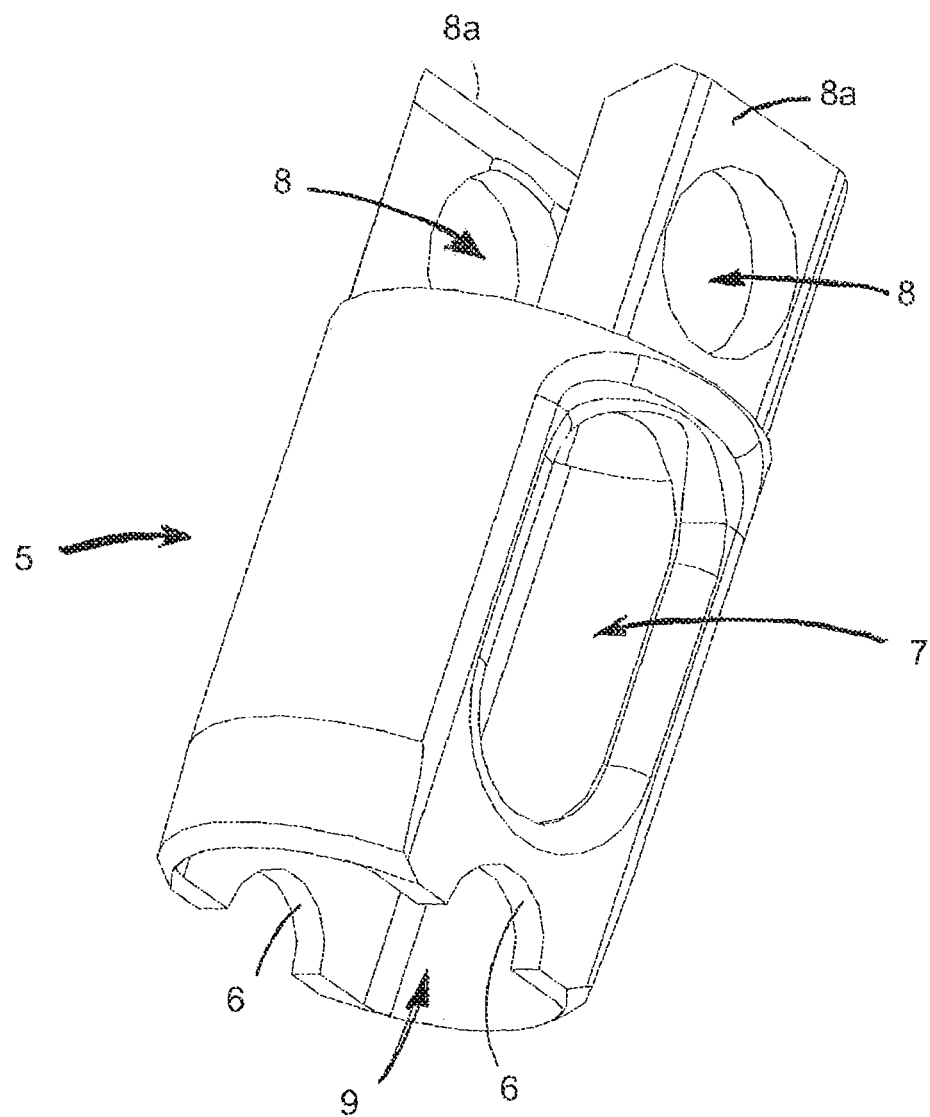
FIG. 4 is an enlarged view of a head portion of the instrument shown in FIGS. 1-3.

FIG. 4 shows the reducer head portion 5 of the reducer instrument. This head portion 5 is designed to abut a spinal rod or other elongate member and drive that elongate member into a coupling device that is held between the two prongs 21 of the clamp member 20. As discussed above, the head portion 5 includes a reducing surface 6 at one end contoured to receive the spinal rod or other elongate member. In the illustrated embodiment, this reducing surface is formed as a concave semi-circle or a semi-cylindrical surface. It is possible, however, for the reducing surface to have a variety of shapes and sizes. The opposite end of the head portion 5 is designed to be secured to the reducing sleeve 10. The deflection pins 14 are positioned through openings in the reducing sleeve 10 and also in the circular openings 8 of the reducer head portion 5. The circular openings 8 are positioned within tabs 8a or a similar structure that may slide into or over the reducer sleeve 10. The reducer head portion 5 also includes an axial bore 9 that is shaped and sized to receive a coupling device held between the clamping prongs 21. A window 7 is provided in each side of the reducer head portion 5 in order to allow the user to see the coupling device that is held by the instrument even when the reducer head portion 5 is in the fully extended position. In order to allow for a visualization of the coupling device, the clamping member prongs 21 are arranged in either side of the window 7, so that the gap 23 between the prongs 21 is aligned with the window 7.

Movement of the reducer sleeve in the illustrated embodiment is regulated by a ratchet mechanism, which may be engaged in order to prevent retrograde motion of the reducer sleeve and reducer head portion. When the ratchet mechanism is engaged, it allows the drive member 30 to be rotated in only one of a clockwise and counterclockwise direction, and prevents rotation in the opposite direction. Reverse rotation of the drive member 30 is prevented by the interaction of the annular arrangement of the ratchet teeth 52 of the drive member 30 and a pawl mechanism coupled to the clamping member 20 in which the drive member 30 is located (see FIGS. 2 and 3). The portions of the ratchet mechanism that are coupled to the clamping member 20 include a ratchet housing 53, a ratchet arm 54, and a ratchet pawl 55. The ratchet arm 54 and ratchet pawl 55 are held within the ratchet housing 53 as explained below. An annular ratchet cover 58 is designed to surround the upper portion of the ratchet housing 53 to cover the elements of the ratchet mechanism. Furthermore, rotation of the ratchet cover 58 serves to engage and disengage the ratchet mechanism by selectively forcing the ratchet arm and associated pawl toward the ratchet teeth.

Figure 5:
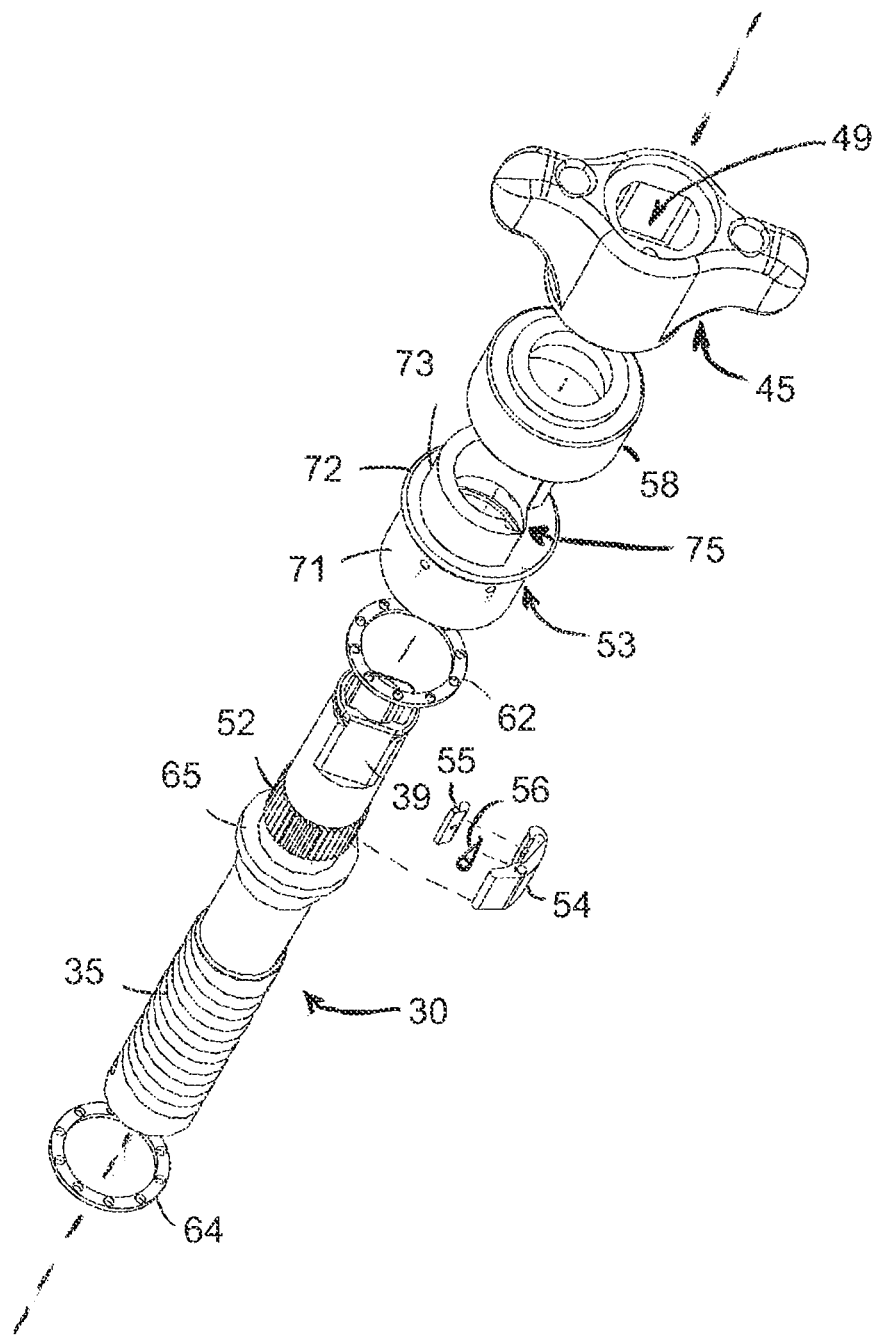
FIG. 5 is an exploded perspective view of the ratchet subassembly of the instrument of FIG. 1.
Figure 6:
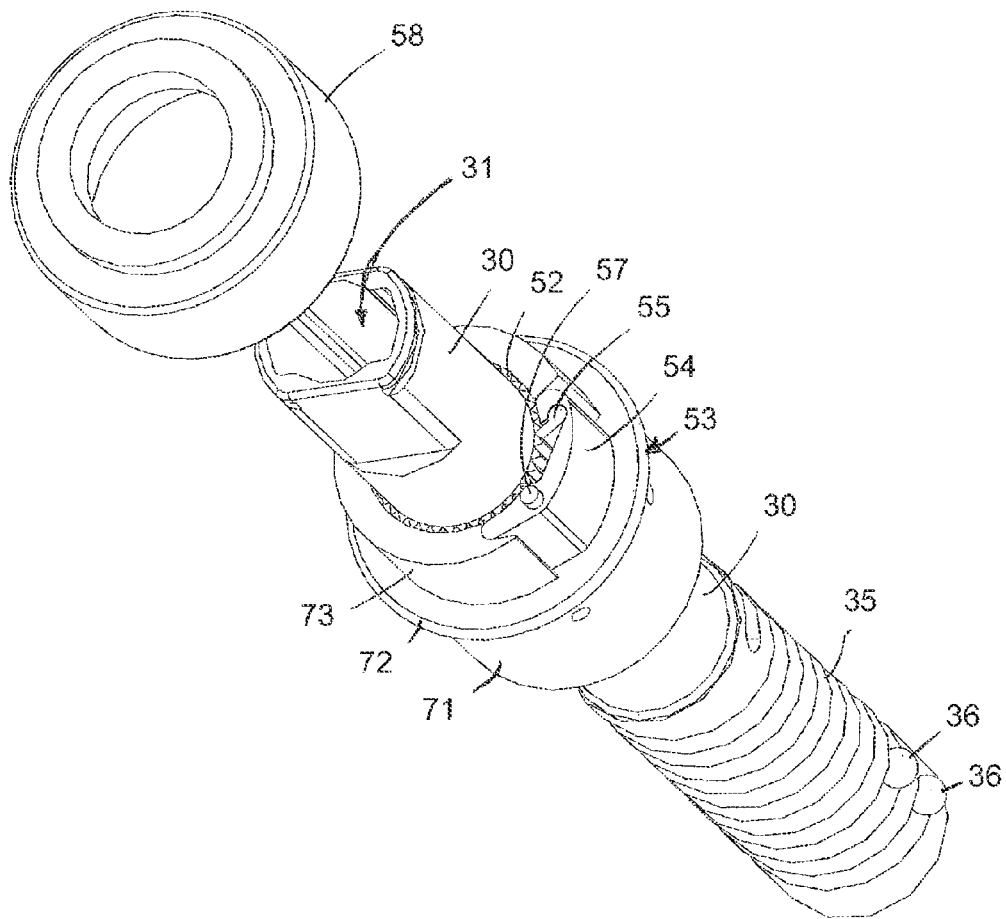
FIG. 6 is a perspective view of the partially assembled ratchet subassembly of FIG. 5 with a ratchet cover removed.

As seen in FIGS. 5 and 6, the ratchet housing 53 is disposed about the annular ratchet 52 in the assembled instrument, and rests above the annular flange 65 of the drive member 30. An array of ball bearings 62 is disposed above the annular flange 65 and below a surface of the bearing housing 53. The ball bearing array 62 may be held in place by a circular bearing retainer 61. When the ratchet housing 53 is fixed with respect to the clamp member 20, such as by welding the two components together, the bearing array 62 facilitates rotation between the drive member 30 carrying the annular ratchet teeth 52 and the ratchet housing 53 that carries the ratchet arm 54 and ratchet pawl 55.

The bearing housing 53 includes a base member 72 that rests above the annular flange 65 of the drive member 30 and the bearing array 62 designed to facilitate rotation between the drive member 30 and the ratchet housing 53. Extending downward from the base member 72 is an annular wall 71. This annular wall 71 covers the bearing arrays 62 and 64 that are adjacent to annular flange 65 of the drive member 30, and the annular wall 71 may be welded to the clamp member 20 (see FIGS. 2-3) in order to seal off the bearing arrays 62 and 64. The portion of the ratchet housing 53 above the base member 72 forms a c-shaped wall 73, which is essentially an annular wall with a gap 75 disposed therein. Gap 75 provides space for the ratchet arm 54 to be situated therein, adjacent the annular ratchet teeth 52 of the drive member 30. The ratchet arm 54 is connected to a post member 57 that is taller than the ratchet arm and interacts with an upper surface of the interior of the ratchet cover 58. The post member and the configuration of the c-shaped wall 73 allow the ratchet arm 54 to pivot toward and away from the center of the ratchet housing 53, in which the annular ratchet teeth 52 are disposed when instrument is assembled. The ratchet cover 58 is disposed around the c-shaped wall 73 of the ratchet housing 53 and also serves to contain the ratchet arm 54 and associated ratchet pawl 55. The outer wall of the ratchet cover limits the movement of the ratchet arm 54 away from the annular teeth 52.

The ratchet housing 53, ratchet arm 54, ratchet pawl 55, and post 67 are shown in FIG. 6 in position relative to the drive member 30 and the annular array of ratchet teeth 52 provided thereon in order to form the majority of the ratchet assembly. The ratchet cover 58 slides down around the top end of the drive member 30 and around the c-shaped wall 73 of the ratchet housing 53 in order to complete the ratchet assembly. In its final position, the ratchet cover 58 sits atop the base member 72 of the ratchet housing 53 and may be rotated relative to the ratchet housing 53 in order to engage and disengage the ratchet mechanism. In particular, as will be explained below, rotation of the ratchet cover 58 in one direction holds the ratchet arm 54 against the annular teeth 52 so that the ratchet pawl 55 is forced to engage the teeth 52 and allow them to pass in only one direction, allowing the drive member 30 to rotate in a first direction but preventing the drive member 30 from rotation in a second opposite direction. When the ratchet cover 58 is rotated in the opposite direction to a second position, the ratchet arm 54 is allowed to fall away from the ratchet teeth 52, so that the pawl 55 no longer is tightly engaged to the annular ratchet teeth 52 and allowed them to pass when the drive member 30 is rotated in either a clockwise or counterclockwise direction.

Ordinarily, a pivotable ratchet pawl is disengaged by simply pivoting the contact points away from the ratchet teeth, allowing the teeth to pass unhindered by the disengaged pawl. However, since the pawl prevents backward movement of the ratchet teeth by binding against the rear surfaces of the teeth, the ratchet teeth must normally be advanced by a slight amount in order to relieve any binding between the pawl and the teeth, providing the pawl with room to pivot out of the way. In other words, the load placed on the ratchet mechanism by the forces which the ratchet mechanism is designed to resist must ordinarily be relieved before the ratchet pawl can be pivoted away from the ratchet teeth to disengage the ratchet mechanism. In the instrument shown in FIGS. 1-11, however, this is problematic because it is of great advantage for the ratchet mechanism to be able to hold the reducer member in a fully advanced state, and further advancement to disengage the ratchet mechanism would ordinarily be impossible at that point. However, the ratchet mechanism shown in FIGS. 5 and 6 solves this problem by mounting the ratchet pawl 55 to a moveable arm 54 so that the entire pawl can be shifted away from the array of ratchet teeth 52 to disengage the ratchet mechanism instead of simply pivoting the pawl mechanism. Thus, by mounting the pawl 55 to a moveable ratchet arm 54, the ratchet mechanism has the ability to engage and disengage without further advancement of the reducer member even when under a heavy load. The reducer sleeve 10 of the instrument may therefore be released directly from a fully extended position without exerting additional forward force on the reducer sleeve that could potentially damage the spinal rod that it is reducing.

Figure 7:
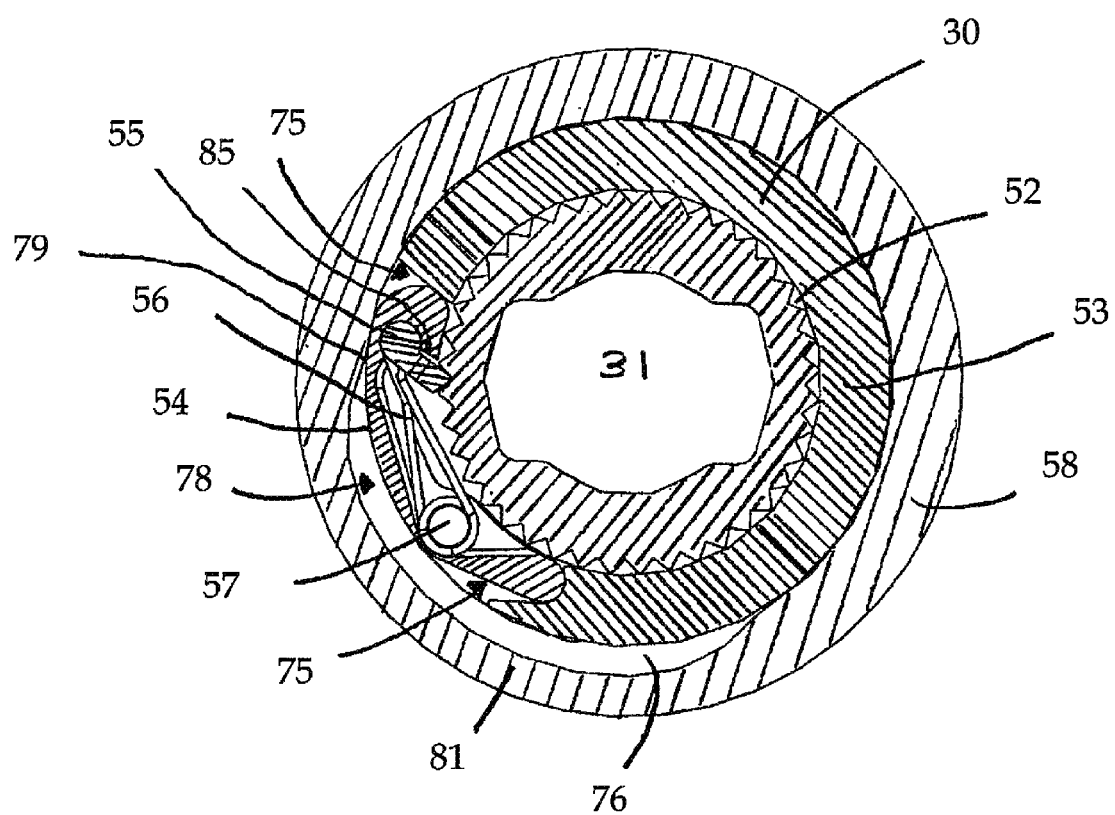
FIG. 7 is a cross-sectional view of the ratchet subassembly shown in FIGS. 5 and 6.
Figure 8:
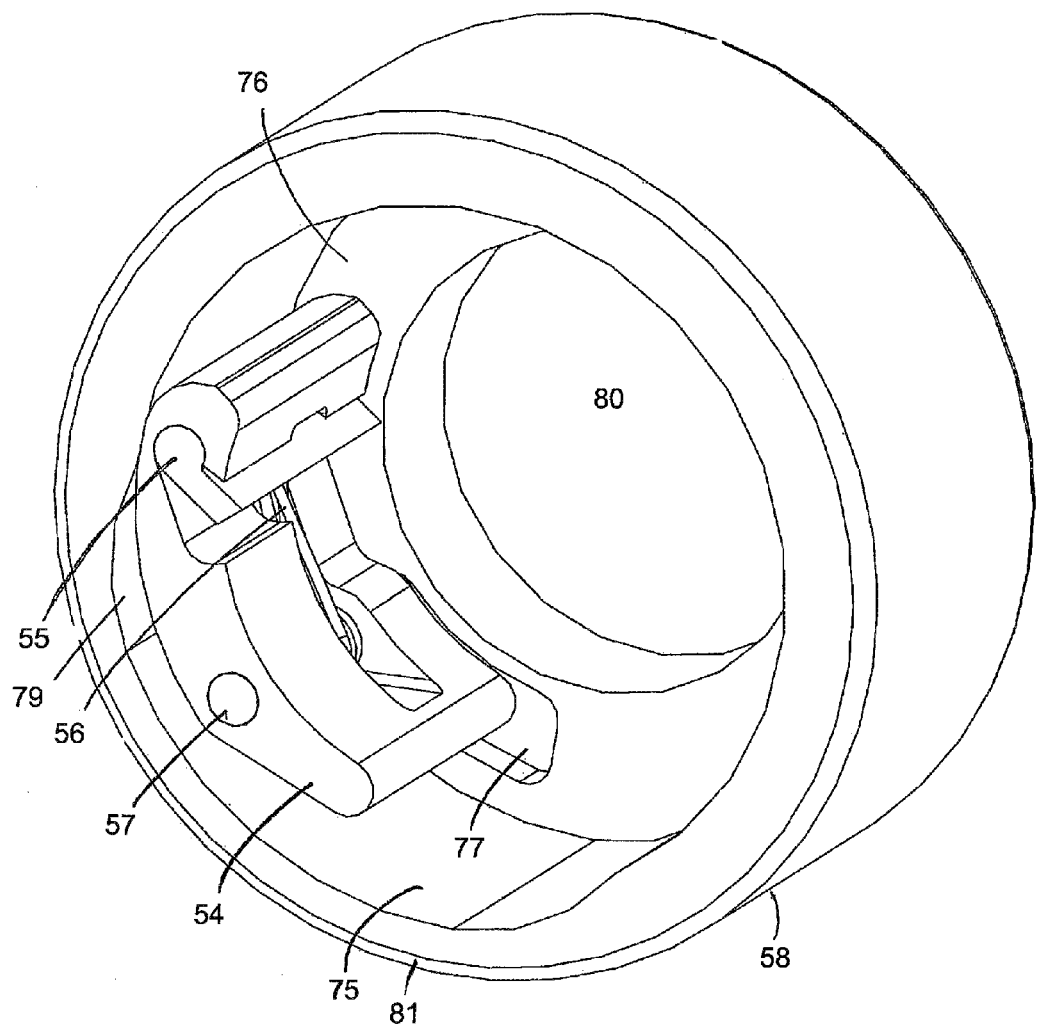
FIG. 8 is a perspective view of the interior of the ratchet cover with a ratchet arm and pawl positioned therein.

FIGS. 7 and 8 depict the ratchet cover 58 from below, with the ratchet arm 54 and the ratchet pawl 55 in place and in an engaged position. The drive member 30 with the associated array of the annular ratchet teeth 52 (see FIG. 6) normally would be disposed through the opening 80 in the ratchet cover 58. The ratchet arm 50 and ratchet pawl 55 are designed to rest adjacent to the ratchet teeth. The ratchet cover 58 includes an upper wall 76 and an annular outer wall 81. The thickness of the outer wall 81 varies so that rotation of the ratchet cover 58 engages and disengages the ratchet arm 54 with the annular teeth of the drive member. Where the outer annular wall 81 is thinnest, a recess or space 78 is created that allows the ratchet arm 54 to pivot outwardly and away from the annular teeth at the center of the ratchet mechanism. As the ratchet cover 58 is rotated into an engagement position, a shoulder 79 of the inner wall 75 begins to engage the pivotable ratchet arm 54 and forces the arm inward so that the ratchet pawl 55 cradled by the ratchet arm 54 abuts the ratchet teeth. The ratchet pawl is allowed to swing in one direction (clockwise as viewed from below) to allow the ratchet teeth to pass, but attempts to rotate the ratchet teeth in the opposite direction are prevented to the interaction of the ratchet pawl 55 and an abutment surface 85 created by the shape of the ratchet arm 54 that holds the pawl. A ratchet spring 56 disposed within the arm 54 biases the pawl 55 into a position wherein the pawl engages the ratchet teeth, but allows the pawl to pivot outward into a notch 86 in the arm 54 in order to allow the ratchet teeth to pass by. It will be understood that when the ratchet cover 58 is positioned so that the space 78 formed by the thinning of the outer wall is adjacent the free end 87 of the ratchet arm 54, rotation of the ratchet teeth in a direction that forces the pawl 55 against the abutment surface 85 of the arm 54 will simply cause the entire arm 54 to pivot outwardly, shifting the free end 87 of the arm out into the open space 78 and letting the ratchet teeth pass by the pawl unobstructed. As previously mentioned, without the moveable ratchet arm 54, release of the ratchet mechanism would require rotation of the ratchet teeth 52 in a counterclockwise direction (as viewed in FIG. 7) until the pawl 55 had sufficient room to pivot clockwise out of the way of the teeth. By mounting the pawl 55 in a ratchet arm 54 that is itself pivotable or otherwise moveable, the ratchet mechanism may be released from any given point, even when a significant force biases the ratchet teeth 52 in a clockwise direction.

A post slot 77 (FIG. 8) forms an arc in the upper wall 76 of the ratchet cover 58 and directs the post 57 to slide therein to shift the position of the arm 54 as the ratchet cover 58 rotates from an engagement position to a disengagement position and back again. In other words, the shape and direction of the slot 77 cause shifting of the post 57 as the ratchet cover 58 is rotated, which in turn causes the ratchet arm 54 to pivot toward and away from the ratchet teeth. Alternatively, the arm may be configured to be shifted solely by forces exerted by rotation of the ratchet teeth that push the arm outward.

Figure 9:
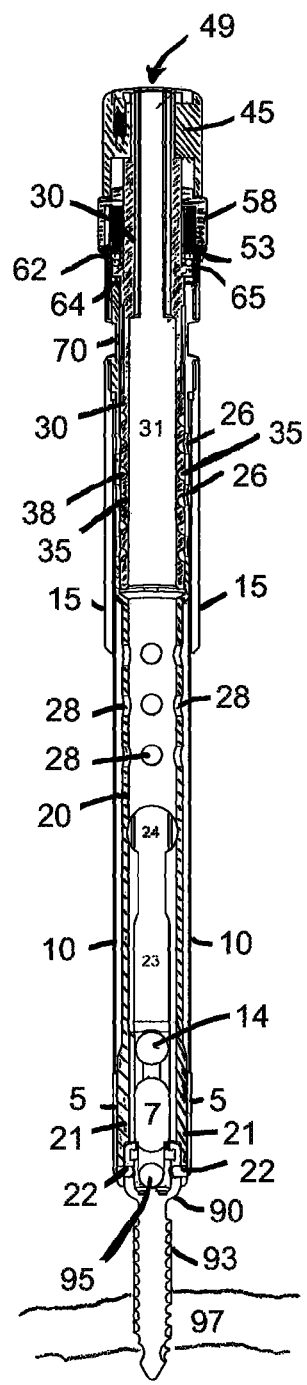
FIG. 9 is a cross-sectional view of the instrument of FIG. 1.
Figure 10:
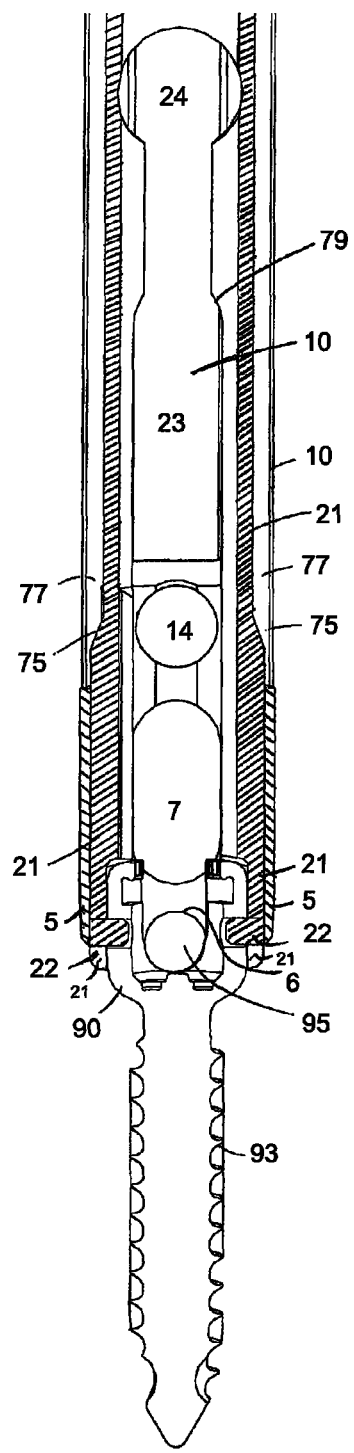
FIG. 10 is a magnified view of the distal portion of FIG. 9.
Figure 11:
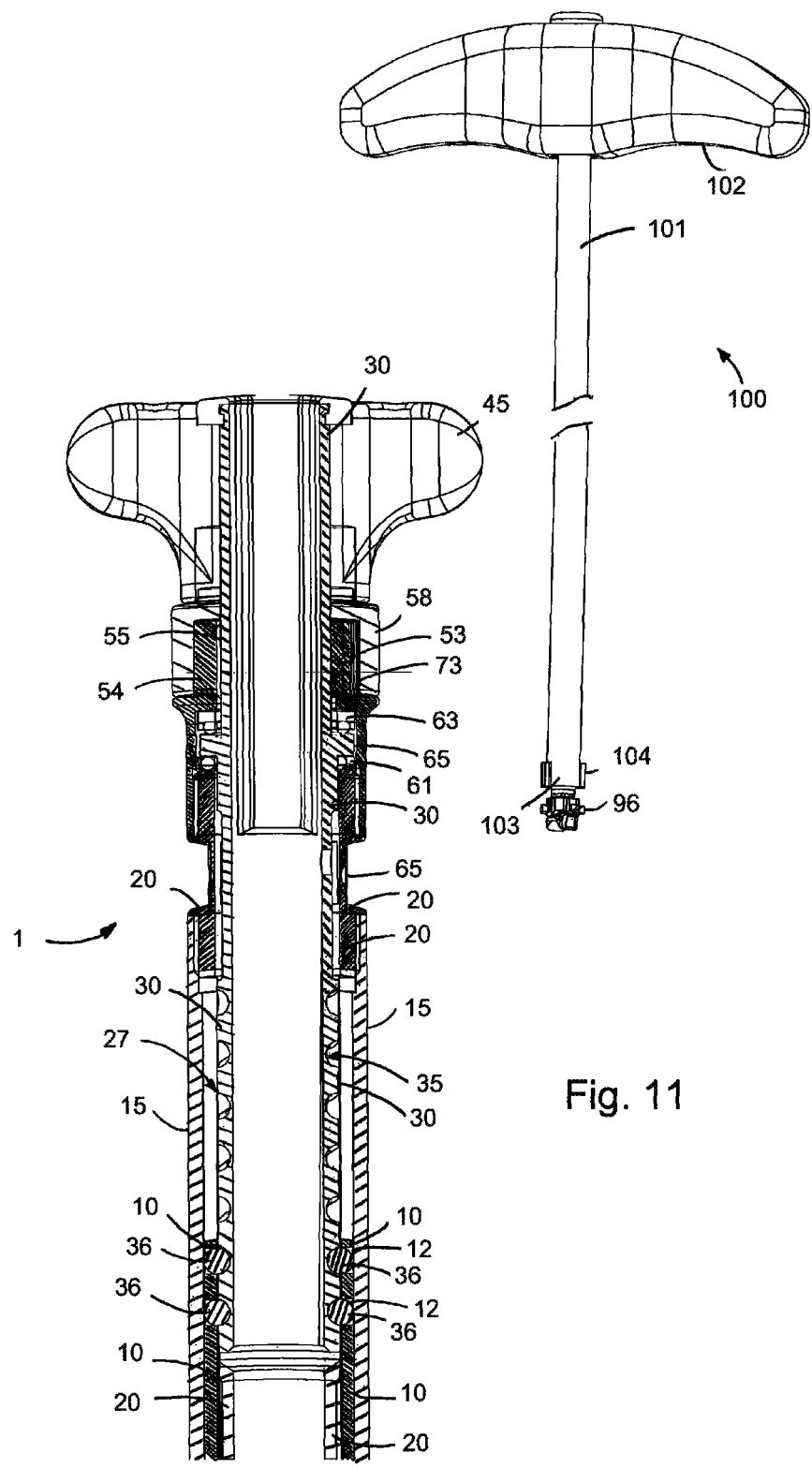
FIG. 11 is a magnified view of the proximal portion of FIG. 9.

FIGS. 9 through 11 show cross sectional views of the instrument of FIG. 1. FIG. 9 is a cross section view of the entire reducer instrument of FIG. 1 grasping a representative coupling device 90 and reducing a spinal rod 95 into the device 90. The illustrated coupling device 90 includes a shank or screw portion 93 that is driven into a boney surface 97 of a vertebra. The device 90 alternatively may be secured by other means to vertebra, such as by a hook or a wire. The clamp member prongs 21 of the instrument surround the coupling device 90 on both sides, and holding pegs 22 interface with complimentary openings or indentations on either side of the coupling device 90.

As shown in the magnified view of FIG. 10, the reducer head portion 5 is disposed about the exterior of the clamping prongs 21. As best seen in FIG. 10, the reducer head 5 lies below the reducer sleeve 10, as coupled thereto by pin 14. The reducer head portion 5 fits tightly around the clamp prongs 21 holding the coupling device 90 to the lower portion of the prongs 21. However, there is adequate space 77 between the clamping prongs 21 and the reducer sleeve 10 and/or reducer head portion 5 toward the top of the clamp members 21 that when the reducer sleeve 10 and reducer head portion 5 are retracted above the shoulder portion 75 of the clamp prongs 21 they do not interfere with lateral splaying of the clamping prongs 21. This lateral splaying allows the coupling device 90 to be received between and removed from the clamping prongs 21. The reducer sleeve 10 and reducer head 5 shift downward to abut the shoulder portion of the clamping prongs 21 and then slide snugly around the exterior of the clamping prongs, preventing any outward splaying of the clamping prongs 21 and holding the prongs tightly to the coupling device 90. In order to release the coupling device 90, the reducer head portion 5 and reducer sleeve 10 are retracted, sliding upward past the clamping prong shoulder portion to permit outward splaying of the clamping prongs 21. Simultaneously, the pin 14 holding the reducer head portion 5 to the reducer sleeve 10 shifts upward and will abut the ramp portion 79 formed by the narrowing of the gap 23 between the clamping prongs 21. Abutment of the pin 14 against the ramp portion will force the clamping prongs apart, releasing the coupling device 90.

FIG. 11 is a magnified cross sectional view of the ratchet mechanism and the drive mechanism of the reducer instrument. The drive actuator handle 45 is fixed to the drive member 30, with the drive member 30 is rotatably inserted into the clamp member 20. The annular flange 65 of the drive member 30 rests above the top end of the clamping member 20 with a bearing array 61 disposed between the annular flange 65 and clamping member 20 in order to facilitate rotation between the two. The drive member 30 is coupled to the reducer sleeve 10 disposed about the exterior of the clamping member 20 by force rolling spherical element 36 that are partially disposed in a helical groove 35 of the drive member 30 and openings 12 of the reducer sleeve 10. A vertical slit 27 in the clamping member 20 allows the rolling spherical elements 36 to contact both the drive members 30 and the reducer sleeve 10 despite the clamping member 20 being disposed between the two. The helical groove 35 of the drive member may have a varied pitch so that a given degree of rotation of the drive member results in a different amount of linear shifting of the reducer member 10 depending on the positioning of the reducer member. For instance, the pitch of the groove 35 may become shallower toward the distal end of the drive member so that as the reducer sleeve approaches its fully extended position the reducer sleeve advances more slowly and provides the surgeon with a greater mechanical advantage, allowing the surgeon to more easily make fine adjustments at the end of the reducing procedure.

A cover sleeve 15 is fixed to the clamping member 20 and covers the portion of the reducer sleeve 10 containing the rolling spherical elements 36. This protects the rolling spherical elements and other components of the drive mechanism from dirt and debris. The cover sleeve 15 may be secured to the clamping member 20 by welding, adhesive, or other means.

As discussed previously, rotation of the drive member 30 may be selectively limited by a ratchet mechanism. FIG. 11 also illustrates the ratchet mechanism shown in FIGS. 5-8. The ratchet housing 53 is mounted to the upper end of the clamping member 20 and prevents the drive member 30 from moving vertically due to interference between the annular flange 65 of the drive member and the inner surface of the housing 53. An array of ball bearings 63 is disposed between the two in order to facilitate rotation of the drive member 30. The upper wall 73 of the ratchet housing 53 is c-shaped to accommodate a ratchet arm 54 on one side of the instrument. A rotatable ratchet cover 58 is disposed about the upper c-shaped wall 73 of the ratchet housing 53, and maintains the ratchet arm 54 in position. Selective rotation of the ratchet cover 58 engages and disengages the ratchet arm 54 with teeth 55 disposed about the drive member 30, as previously discussed.

In order to lock the elongate member to the coupling member 90 once the instrument has been used to reduce the elongate member, a locking member inserter may be provided. Since the full interior of the illustrated instrument is cannulated, as best shown in FIG. 9, the locking member inserter may be inserted through the opening 49 at the proximal end of the instrument and downward through the axial through bore formed through the instrument.

One exemplary locking member inserter 100 is illustrated in FIG. 11, and includes an elongate body 101 long enough to reach the coupling device 90 through the entire length of the cannulated interior of the reducer instrument 1. The locking member inserter 100 also has a head portion 103 that holds a locking member 96 in position in order to introduce the locking member 96 into the coupling device 90. The locking member inserter may contain a handle to assist the surgeon in locking the locking member. For instance, if the locking member must be rotated to a locked position within the coupling device 90, a T-shaped handle such as the illustrated handle 102 may be provided at the end of the inserter to provide the surgeon with a mechanical advantage for rotating the inserter 100 and locking member 96. In addition, in some instances the inserter 100 will be provided with wings 104 or other structures to guide the alignment of the inserter and locking member 96. The wings 104 would be designed to interact with structures (such as guide channels) in the interior of the reducer instrument 1 to align the locking member 96 properly with the coupling device 90 held by the reducer instrument 1.

It is intended for the following claims to cover these and any other departures from the disclosed embodiment which fall within the true spirit of the invention.

What is claimed is:

1. An instrument for reducing a spinal rod, the instrument comprising:
    an elongate clamp member having an axial throughbore and configured for holding a coupling member of a spinal fixation system;
    a rotatable drive member distinct from the clamp member, and sized to be received in the clamp member axial throughbore to be rotatably coupled to the clamp member, the drive member including a helical groove;
    at least one rolling ball element partially disposed in the helical groove of the drive member;
    an elongate reducer member configured to be linearly shifted with respect to the clamp member, the reducer member including at least one opening sized and configured to receive the at least one rolling ball element such that rotation of the drive member causes the reducer member to be linearly advanced by converting an input rotary drive force applied to the rotatable drive member to translatory motion of the elongate reducing member along the elongate clamp member with the rolling ball element transmitting drive forces therebetween to provide a low friction drive interface between the drive member and the reducer member; and
    a one-way locking mechanism that is operable to maintain the reducer member in a distally advanced position thereof by restricting proximal linear shifting thereof.

2. The instrument of claim 1 wherein the one-way locking mechanism is a ratchet mechanism that selectively inhibits rotation of the drive member in at least one direction, the ratchet mechanism including a plurality of ratchet teeth, a pivotable pawl configured to interact with the ratchet teeth, and a moveable ratchet arm coupled to the pawl that shifts the pawl toward and away from the ratchet teeth to engage and disengage the one-way locking mechanism.

3. The instrument of claim 1 wherein the reducer member is a sleeve disposed about the clamp member.

4. The instrument of claim 1 wherein shifting of the reducer member causes clamping and unclamping of the clamp member.

5. An instrument for reducing a spinal rod comprising:
    an elongate clamp member for receiving a coupling member of a spinal fixation system, the clamp member comprising a hollow, generally cylindrical first end and a second end comprising a plurality of clamping arms, the generally cylindrical first end having at least one elongate slit disposed therein;

a drive member rotatably disposed in the generally cylindrical first end of the clamp member, the drive member including a helical groove extending thereabout;

at least one rolling element partially disposed in the helical groove of the drive member and partially disposed within the elongate slit of the clamp member;

an elongate reducer sleeve disposed about the clamp member and configured to be linearly shifted with respect to the clamp member, the reducer member including at least one opening sized and configured to receive the at least one rolling element; and a one-way locking mechanism comprising:

an annular array of ratchet teeth coupled to the exterior of the drive member;

a ratchet pawl disposed adjacent to the ratchet teeth; and a ratchet control member that holds the ratchet pawl against the ratchet teeth when shifted to a first position and allows the ratchet pawl to shift away from the ratchet teeth when the control member is shifted to a second position;

wherein rotation of the drive member causes linear shifting of the reducer sleeve due to the interaction between the helical groove, the rolling element, and the reducer sleeve; and wherein the one-way locking mechanism allows rotation of the drive member in two directions when the control member is in the first position but allows rotation of the drive member in only one direction when the control member is in the second position.

6. The instrument of claim 5, wherein the helical groove of the drive member has a varied pitch along the length of the drive member to automatically adjust the amount of linear shifting of the reducer sleeve accomplished with a given amount of rotation of the drive member depending upon the linear position of the reducer member.

7. The instrument of claim 5, wherein the ratchet control member is an annular structure surrounding the ratchet teeth and ratchet pawl, with an interior surface contoured so that rotating the annular structure to a first position maintains the position of the ratchet pawl in close enough proximity to the ratchet teeth to prevent rotation of the teeth in one direction and so that the ratchet pawl has room to shift away from the ratchet teeth when the control member is rotated to a second position.

8. The instrument of claim 5, further comprising pins associated with the reducer sleeve and disposed between the clamping arms, wherein the clamping arms are shaped so that movement of the reducer sleeve and associated pins in one direction forces apart the clamping arms for receiving a coupling member therebetween.

9. The instrument of claim 5, further comprising a locking member insertion instrument disposable within the drive member and clamping member and capable of interacting with a coupling member when the coupling member is held between the clamping arms.

* * * * *